United States Patent [19]

Aldrich

[11] Plant 4,053

[45] May 10, 1977

[54] PLUM TREE

[75] Inventor: Susan A. Aldrich, Mukilteo, Wash.

[73] Assignee: Stark Bro's Nurseries & Orchards Co., Louisiana, Mo.

[21] Appl. No.: 679,506

[22] Filed: Apr. 22, 1976

[51] Int. Cl.[2] ..... A01H 5/03
[52] U.S. Cl. ..... Plt./38
[58] Field of Search ..... Plt./38

[56] References Cited

OTHER PUBLICATIONS

Register of New Fruit & Nut Varieties, 2nd Ed., Brooks et al., 1972, U of CA press, p. 492.

*Primary Examiner*—Robert E. Bagwill
*Attorney, Agent, or Firm*—Burns, Doane, Swecker & Mathis

[57] ABSTRACT

This invention relates to a new and distinct variety of plum tree which most nearly resembles the "Italian Prune" tree (unpatented). In contrast to this known tree the new variety has (a) resistance to fungal and bacterial leaf spots, (b) a more spreading growth habit, (c) larger fruit, and (d) earlier ripening fruit.

1 Drawing Figure

DESCRIPTION OF NEW VARIETY

The present new and distinct variety of plum tree was found about 1940 as a seedling growing in a cultivated area. More specifically, the new variety was found among seedling "Italian Prune" trees growing at Bothell, Snohomish County, Wash. The pollen parent of the new variety is unknown.

Because of the distinctive characteristics of the new variety the plant was asexually reproduced during 1951 by budding onto *Prunus cerasifera* understock near Louisiana, Mo. on property of the assignee. The specimens described herein were grown and observed near Louisiana, Mo.

The drawing is representative of the fruit and a branch with leaves of the new and distinct variety.

The new variety closely resembles the "Italian Prune" tree with the exception that it (a) has increased foliage resistance to diseases such as fungal leaf spot and bacterial leaf spot, including Coccomyces leaf spot, (b) the tree is more spreading, (c) the fruit is larger, and (d) the fruit ripens earlier. Also, the fruit is considered to be of better flavor than that of the "Italian Prune".

The disease resistance of the new variety has been confirmed by observing the variety over a period of years beginning in 1953 to date while growing in a test orchard near Louisiana, Mo., where diseases such as "leaf blight" caused by *Coccomyces prunophorea* (Higgins) and "bacterial spot" caused by Pseudomonas pruni (E. F. Smith) were active and encountered in many other nearby varieties including the "Italian Prune".

The new variety possesses an unusually spreading growth habit, even more so than the "Italian Prune", which itself is more spreading than the European varieties.

The new variety ripens approximately 17 days earlier than the "Italian Prune", and approximately 10 days earlier than the "Brooks Italian Prune".

Dates first and last picking: Aug. 25th–Aug. 31st.

The following is a detailed description of my new variety:

Tree: Medium-large size; vigorous; dense; spreading; round topped; hardy; productive.

*Trunk.*—Stocky.

*Branches.*—Medium slender; smooth; brown (Mummy Brown Plate XV, Color No. 17′, tone *m* of Ridgway's Color Standards and Nomenclature).

*Lenticels.*—Numerous; small.

*Leaves.*—Length — 4 inches; width 1⅞ to 2½ inches. Medium to large size; oval; abruptly pointed; thick; dark green (Parsley Green — Color No. 00962/2, Vol. 2 — Page 193 Horticulture Colour Chart); rugose. Margin — glandular; crenate. Petiole — medium to long length (about ⅞ inch). Glands — small size; globose; appressed; average number 1.

*Flowers.*—Dates first and full blossom — Apr. 10th–Apr. 15th; medium late; medium to large size; white.

Fruit: Maturity when described — eating ripe. Date — Sept. 1st.

*Size.*—Uniform; medium — large. However, the size of the fruit tends to vary inversely with the size of the crop for a given year. For instance, during 1975 when the trees had a very heavy crop despite late freezes which reduced the production of all other varieties in the area the dimensions of the fruit are as indicated hereafter. Axial diameter 2⅛ inches. Transverse in suture plane 1½ inches. At right angles to suture plane 1½ inches.

*Form.*—Uniform; symmetrical; broadly ovoid. Suture — distinct; extends from base to apex. Ventral surface — slightly lipped toward base; lips equal. Cavity — abrupt circular; suture showing on one side. Depth 5/32 inch; breadth ¼ inch. Base — cuneate. Apex — rounded. Pistil point — apical. Stem — medium stout; pubescent. Adherence to stone — weak to medium. Skin — medium thick; medium tough; astringent; tenacious to flesh. Tendency to break — none in wet or dry season. Color — Dusky Slate Violet (Plate XLIII, Color No. 57‴, tone *m*) with Pale Grayish Violet Blue bloom (Plate XXIV, Color No. 53, *d*, both of Ridgway's Color Standards and Nomenclature).

*Flesh.*—Color — Sea-foam Green (Plate XXXI, Color No. 27″, tone *f* of Ridgway's Color Standards and Nomenclature). Surface of pit cavity color — Clear Dull Green Yellow (Plate XXVII, Color No. 25″, tone *b* of Ridgway's Color Standards and Nomenclature).

*Amygadalin.*—Wanting. Juice — moderate, rich.

*Texture.*—Meaty.

*Fibres.*—Few, fine, tender.

*Ripens.*—Fairly evenly; earliest at pit.

*Flavor.*—Subacid, vinous.

*Aroma.*—Distinct.

*Eating quality.*—Good.

Stone: Semi-free; adheres to flesh along ventral edges.

*Fibres.*—Short; free towards base; retains short fibre like threads along edges.

*Size.*—Small to medium; length 1-1/16 inch; thickness 5/16 inch.

*Form.*—Oval; cuneate toward base of apex.

*Base.*—Oblique. Hilum — narrow. Apex — rounded.

*Sides.*—Equal; flattened.

*Surface.*—Irregularly furrowed near ventral edge; pitted throughout; ridges rounded.

*Pits.*—Ventral edge — thin without wing.

*Dorsal Edge.*—Full with shallow groove throughout. Ridges on either side continuous.

Use: Market; dessert; canning.

Keeping quality; Medium to good.

Resistance to Diseases: Good. Is particularly resistant to Coccomyces leaf spot and bacterial leaf spot.

Shipping quality: Good.

Having thus described and illustrated my new variety of plum tree, what is claimed as new and desired to be secured by Letters Patent is:

1. A new and distinct variety of plum tree, substantially as illustrated and described, which most nearly resembles the "Italian Prune" tree (unpatented), but from which it is distinguished by resistance to fungal and bacterial leaf spots, a more spreading growth habit, larger fruit, and earlier ripening fruit.

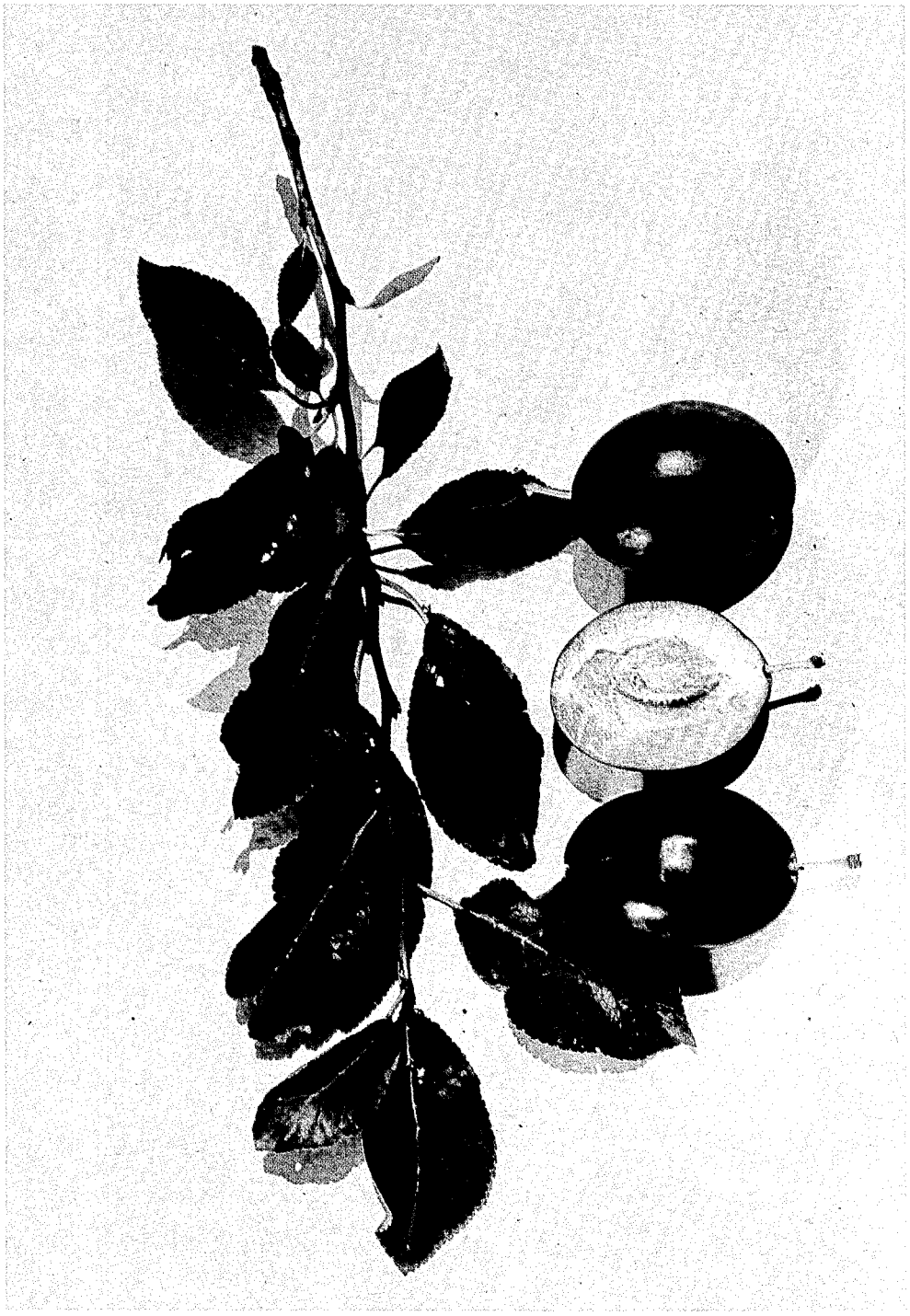

* * * * *